United States Patent
Sen et al.

(10) Patent No.: US 6,344,594 B1
(45) Date of Patent: Feb. 5, 2002

(54) HIGHLY SELECTIVE CATALYTIC PROCESS FOR SYNTHESIZING 1-HEXENE FROM ETHYLENE

(75) Inventors: Ayusman Sen, State College, PA (US); Shahid Murtuza, Chicago, IL (US); Seth B. Harkins, Pasadena, CA (US); Cecily Andes, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/550,089

(22) Filed: Apr. 14, 2000

Related U.S. Application Data

(60) Provisional application No. 60/129,797, filed on Apr. 16, 1999.

(51) Int. Cl.[7] .................................................. C07C 2/08
(52) U.S. Cl. ....................... 585/511; 585/510; 585/512; 585/516
(58) Field of Search ................................ 585/510, 511, 585/512, 516

(56) References Cited

U.S. PATENT DOCUMENTS

| | | | | |
|---|---|---|---|---|
| 4,245,131 A | * | 1/1981 | Schrock | 585/511 |
| 4,476,343 A | * | 10/1984 | Johnson | 585/530 |
| 4,717,783 A | * | 1/1988 | Dubois et al. | 585/511 |
| 4,772,734 A | * | 9/1988 | Dubois et al. | 556/11 |
| 4,777,315 A | | 10/1988 | Levine et al. | 585/512 |
| 5,376,612 A | | 12/1994 | Reagan et al. | 502/104 |
| 5,731,487 A | | 3/1998 | Tamura et al. | 585/513 |
| 5,750,816 A | | 5/1998 | Araki et al. | 585/512 |
| 5,811,618 A | | 9/1998 | Wu | 585/513 |
| 6,150,576 A | * | 11/2000 | Jiang et al. | 585/18 |

OTHER PUBLICATIONS

Riggs, John R., *The Selective Trimerozationof Ethylene to Hex–1–ene*, J. Cehm. Soc., Chem. Commun., 674–675 (1989) –no month.

Manyik, R.M., et al., *A Soluble Chromium–Based Catalyst for Ethylene Trimerization and Polymerization*, J. of Catalysis, 47, 197–209 (1977) –no month.

* cited by examiner

*Primary Examiner*—Nadine Preisch

(57) ABSTRACT

Ethylene is trimerized to form 1-hexene, at a selectivity of up to about 99 mole percent, by contacting ethylene, at an ethylene pressure of from about 200–1500 psig and at a reaction temperature of from about 0° C. to about 100° C., with a catalyst comprising a tantalum compound (e.g., $TaCl_5$) and a alkylating component comprising a metal hydrocarbyl compound or a metal hydrocarbyl halide compound (e.g., $Sn(CH_3)_4$).

11 Claims, No Drawings

HIGHLY SELECTIVE CATALYTIC PROCESS FOR SYNTHESIZING 1-HEXENE FROM ETHYLENE

RELATED APPLICATIONS

This application is based on Provisional Application No. 60/129,797, filed Apr. 16, 1999, and entitled "Highly Selective Ethylene Trimerization Using a Chromium-Free Catalyst."

This invention was funded by a grant from the U.S. Department of Energy, Office of Basic Energy Sciences, Grant No. DE-FG02-84ER 13295

FIELD OF THE INVENTION

The present invention relates to the trimerization of ethylene in the presence of a tantalum-based catalyst to form 1-hexene product at a selectivity of up to about 99 mole percent. Notable characteristics of the present invention are the high selectivity to 1-hexene product, an industrially important product for use as a feedstock for chemical synthesis and as a comonomer for olefin polymerization reactions, and the absence of a need for any chromium catalyst component in the reaction system.

BACKGROUND OF THE INVENTION

The synthesis of 1-hexene from ethylene, an inexpensive and plentiful starting material, generally has been conducted by one of two synthetic routes. In the first route, a variety of metal-based catalytic processes have been reported in which ethylene is oligomerized to produce a relatively wide distribution of products, ranging from butene to much higher oligomers. Included in this distribution can be 1-hexene. However, since several major products are synthesized, they must be separated to obtain pure products, such as 1-hexene. This purification increases production costs and does nothing to increase the selectivity of the product distribution.

In accordance with the second conventional route, several chromium-based catalyst systems have been reported in which ethylene is trimerized to 1-hexene with relatively high selectivity. The route is illustrated, for example, in U.S. Pat. No. 5,376,612 to Reagan et al, in U.S. Pat. No. 5,811,618 to Wu, in U.S. Pat. No. 5,750,816 to Araki et al, in U.S. Pat. No. 5,731,487 to Tamura et al and in U.S. Pat. No. 4,777,315 to Levine et al. A chromium-based catalyst route for trimerizing ethylene to 1-hexene is also illustrated in *J. Catal.* 1977 47 197 and *J. Chem. Soc. Chem. Comm.* 1989 674.

SUMMARY OF THE INVENTION

An object of the present invention is to provide an alternative process for synthesizing 1-hexene from ethylene with a high degree of selectivity.

Another object is to synthesize 1-hexene from ethylene with a high degree of selectivity by trimerizing ethylene in the presence of a catalyst system that does not require the presence of any chromium catalyst component.

Still another object is to provide a tantalum-based catalytic process for synthesizing 1-hexene from ethylene.

These and other objects and advantages of the invention will become apparent from the following detailed description.

DETAILED DESCRIPTION OF THE INVENTION

In contrast with the known chromium-based catalytic processes for synthesizing 1-hexene from ethylene, the present invention provides a process for synthesizing 1-hexene with a high product selectivity by contacting ethylene with a catalytically effective amount of a tantalum-based catalyst composition comprising a tantalum compound, typically a tantalum halide, such as $TaCl_5$ or $TaBr_5$, in combination with an alkylating component comprising a metal hydrocarbyl compound, a metal hydrocarbyl halide compound or an alkyl aluminoxane.

Typically the alkylating component would comprise a lower alkyl metal compound or a loweralkylaryl metal compound, wherein the metal would be selected from the group consisting of tin (Sn), zinc (Zn), aluminum (Al), lithium (Li) or magnesium (Mg). Non-limiting examples of alkylating components that are contemplated for use in this invention include, for example, tetramethyl tin ($Sn(CH_3)_4$), tetraethyl tin ($Sn(CH_2CH_3)_4$), tetraphenyl tin, dimethyl zinc ($Zn(CH_3)_2$), methyl lithium ($LiCH_3$), trimethyl aluminum ($Al(CH_3)_3$), allyl triphenyl tin ($CH_2=CHCH_2Sn(C_6H_5)_3$), triethyl aluminum ($Al(CH_2CH_3)_3$), n-butyl lithium ($Li(CH_3(CH_2)_3)$), dimethyl aluminum chloride ($(CH_3)_2AlCl$), methylaluminoxane (MAO), methyl magnesium bromide ($CH_3MgBr$) or the like.

Generally, the tantalum compound and the alkylating component of the catalyst composition are combined in proportions to provide optimum selectivity to 1-hexene and optimum catalyst activity. Typically, a Ta/alkylating component ratio of from about 0.1 to 10 would be employed. Preferably, the ratio of Ta/alkylating component is from about 0.25 to about 2, and more preferably from about 0.5 to 1.

The synthesis reaction typically would be carried out in a slightly polar, non-coordinating solvent such as toluene, xylene, benzene, chlorobenzene, dichlorobenzene or the like. Aromatic solvents generally are preferred, although catalyst activity has been observed when using halogenated aliphatic solvents such as methylene dichloride, 1,1-dichloroethane, or the like.

The synthesis generally is conducted in batch reactions at pressures and temperatures selected to optimize reaction rates and selectivity. In general, a reaction pressure ranging from about 200 psig to about 1500 psig and a reaction temperature ranging from about 0° C. to about 100° C. would be employed. More typically, the reaction pressure would be on the order of from about 300 psig to about 1000 psig (e.g., 500–1000 psig), and the reaction temperature would be on the order of from about 25° C. to about 70° C. (e.g., 40° C.–60° C.).

When carried out in accordance with this invention, the ethylene trimerization process results in a reaction product containing primarily 1-hexene. Typically the reaction product would contain at least about 50 mole percent of 1-hexene, and more typically at least about 80 mole percent 1-hexene (e.g., from about 80 mole percent to about 99 mole percent). In preferred embodiments, the selectivity to 1-hexene is at least about 94 mole percent, and the reaction product would contain only minor amounts of by-products, such as $C_4$, $C_8$, $C_{10}$ alkenes and higher oligomers. The amount of polyethylene in the reaction product, if any, typically would be negligible.

The invention will be more fully understood and appreciated when considered in light of the following illustrative examples, wherein all catalyst manipulations were carried out in a drybox under a nitrogen atmosphere and all reactions were carried out in a 125mL stainless steel, glass-lined reactor (autoclave) that was disposed in a heated oil bath and equipped with a magnetic stirring means. For each run of each example, the respective reactor was held at the indicated ethylene pressure with constant ethylene feed throughout each run. The actual trimerization reactions were carried out by allowing the reactors to reach the indicated reaction temperature with magnetic stirring for approximately 20 minutes. Then under a purge of ethylene, each reactor was charged with ethylene for the indicated period with magnetic stirring. For each run, the yield of 1-hexene was determined by gas chromatography using chlorobenzene as an internal standard.

EXAMPLE I

Trimerization of Ethylene Using $TaCl_5$ and $Sn(CH_3)_4$ as Catalyst

Trimerization of ethylene, catalyzed by $TaCl_5$ and $Sn(CH_3)_4$, was performed in a 125 mL stainless steel, glass-lined reactor. Tantalum pentachloride (0.018 g/0.05 mmol) was weighed directly into the glass reactor liner to which chlorobenzene (10 mL) was added. Tetramethyl tin (0.013 mL/0.1 mmol) was syringed directly into the solution. The reactor liner was weighed and then placed in the reactor, and the reactor was then closed. The trimerization reaction was carried out as stated above for 4 hours at a temperature of 60° C. After 4 hours, the flow of ethylene was stopped and the reactor was placed in a water/ice bath. After approximately 30 minutes, the reactor was vented. The reactor liner was weighed and a small aliquot of the solution was filtered through a 0.2 µL nylon syringe filter. The yield of 1-hexene, determined by gas chromatography for lower olefms, was 1.018 g with a 96 mole percent selectivity towards 1-hexene and a catalyst activity of 182 turnovers per hour (i.e., yield of hexene/atom of Ta/h). The yield of polyethylene was determined by adding a large excess of methanol to the chlorobenzene solution causing precipitation of high molecular weight polyethylene. Filtration and removal of residual solvents in vacuo resulted in a yield of 0.014 g of solid polyethylene.

EXAMPLE II

Trimerization of Ethylene Using Alkyl Lithium Compound as Alkylating Component Use of alkyl lithium compounds as the alkylating component of the catalyst required isolation of the alkyl lithium from solvent. Methyl lithium (Aldrich, 1.4M in diethyl ether) was isolated by removal of solvent in vacuo using standard Schlenk techniques. Solid methyl lithium (0.022 g/1.0 mmol) was then weighed directly into the reactor liner. Chlorobenzene (10 mL) was then added to the reactor liner. Tantalum pentachloride (0.018 g/0.05 mmol) was then weighed and added to the solution. The reactor liner was weighed and then placed in the reactor, and the reactor was closed. The trimerization reaction was carried out as stated above for 4 hours at 60° C. After 4 hours, the flow of ethylene was stopped and the reactor was placed in a water/ice bath. After approximately 30 minutes, the reactor was vented. The liner was weighed and a small aliquot of the solution was filtered through a 0.2 µL nylon syringe filter. The yield of 1-hexene was 5.016 g with a 91 mole percent selectivity towards 1-hexene and a catalyst activity of 89 turnovers per hour. Gas chromatography was performed to determine the selectivity and yield. The yield of polyethylene was determined by adding a large excess of methanol to the chlorobenzene solution causing precipitation of high molecular weight polyethylene. Filtration and removal of residual solvents in vacuo resulted in a yield of 0.100 g of polyethylene.

EXAMPLE III

Solvent Effects on Trimerization Reaction

In a series of runs, the procedure of Example I was repeated, except that the catalyst components, the reaction temperature, the ethylene pressure, and the solvent were as indicated in Table 1. The selectivity to 1-hexene and the activity (turnovers/h) are also set forth in Table 1.

TABLE 1

| RUN | Catalyst | Solvent | Temp. (° C.) | Ethylene (psig) | Selectivity to 1-Hexene | Activity (turnovers/h)[a] |
|---|---|---|---|---|---|---|
| 1 | $TaCl_5/Sn(CH_3)_4$ | Toluene | 45 | 700 | 97 | 240 |
| 2 | $TaCl_5/Sn(CH_3)_4$ | Toluene | 25 | 700 | 45 | 20 |
| 3 | $TaCl_5/Sn(CH_3)_4$ | Toluene | 70 | 700 | 78 | 260 |
| 4 | $TaCl_5/Sn(CH_3)_4$ | Toluene | 45 | 100 | 74 | 30 |
| 5 | $TaCl_5/Sn(CH_3)_4$ | $C_6H_4Cl_2$[b] | 45 | 700 | 97 | 670 |
| 6 | $TaCl_5/Zn(CH_2CH_3)_2$ | $CH_2Cl_2$[c] | 25 | 700 | 91 | 20 |
| 7 | $TaBr_5/Sn(CH_3)_4$ | Toluene | 45 | 700 | 85 | 120 |
| 8 | $TaBr_5/5\ Sn(CH_3)_4$ | Toluene | 45 | 700 | 90 | 550 |

Conditions: 0.050 mmol $TaX_5$ (X = Cl, Br); 10 mL solvent; 4 h reaction time; 125 mL stainless steel, glass-lined autoclave.
[a]Calculated for 1-hexene only.
[b]$C_6H_4Cl_2$ = 1,2-dichlorobenezene.
[c]$CH_2Cl_2$ = methylene chloride

EXAMPLE IV

Effect of Alkylating Component Concentration on Trimerization Reaction

In a series of runs, the procedure of Example I was repeated, except that the catalyst components, the reaction temperature, and the ethylene pressure were as indicated in Table 2. The selectivity to 1-hexene and the activity (turnovers/h) are also set forth in Table 2. For each run, the solvent was 10 mL of toluene.

TABLE 2

| RUN | Catalyst Components | | Solvent | Temp. (° C.) | Ethylene (psig) | Selectivity to 1-Hexene | Activity (turnovers/h)[a] |
|---|---|---|---|---|---|---|---|
| | Equivalents TaCl$_5$ | Equivalents Zn(CH$_3$)$_2$[b] | | | | | |
| 1 | 1 | 0.50 | Toluene | 45 | 700 | 96 | 173 |
| 2 | 1 | 0.75 | Toluene | 45 | 700 | 97 | 265 |
| 3 | 1 | 1.0 | Toluene | 25 | 700 | 96 | 462 |
| 4 | 1 | 1.5 | Toluene | 70 | 700 | 97 | 277 |
| 5 | 1 | 2.0 | Toluene | 45 | 100 | 43 | 13 |
| 6 | 1 | 3.0 | Toluene | 45 | 700 | 38 | 12 |

Conditions: 0,050 mmol TaCl$_5$; 10 mL toluene solvent; 4 h reaction time; 124 mL stainless steel, glass-lined autoclave.
[a]Calculated for 1-hexene only.
[b]alkylating component.

EXAMPLE V

Effect of Alkylating Component on Trimerization Reaction Selectivity

In a series of runs, the procedure of Example IV was repeated, except that chlorobenzene was used as the reaction solvent and the alkylating component of the catalyst was varied, as indicated in Table 3. The amount of solid product, the selectivity to 1-hexene, and the catalyst activity (turnovers/h) are also indicated in Table 3 for each run.

TABLE 3

| RUN | Ta Compound (0.05 mmol) | Alkylating Component (Equivalents) | Solid Product (grams) | Ethylene (psig) | Selectivity to 1-Hexene | Activity (turnovers/h)[a] |
|---|---|---|---|---|---|---|
| 1 | TaCl$_5$[b] | 2 CH$_3$Li | 0.100 | 700 | 91 | 89 |
| 2 | TaCl$_5$[c] | 1 CH$_3$(CH$_2$)$_3$Li | Trace | 700 | 95 | 21 |
| 3 | TaCl$_5$[d] | 2 CH$_3$(CH$_2$)$_3$Li | — | 700 | 99 | 197 |
| 4 | TaCl$_5$ | 2 C$_6$H$_5$Li | Trace | 700 | 99 | 5 |
| 5[e] | TaCl$_5$ | 2 Sn(CH$_3$)$_4$ | Trace | 700 | 94 | 383 |
| 6 | TaCl$_5$ | 2 Sn(CH$_2$CH$_3$)$_4$ | Trace | 700 | 98 | 39 |
| 7 | TaCl$_5$ | 1 Sn(C$_6$H$_5$)$_4$ | 0.430 | 700 | 26 | 2 |
| 8 | TaCl$_5$ | 2 (allyl)Sn(C$_6$H$_5$)$_3$ | — | 700 | 96 | 590 |
| 9 | TaCl$_5$ | 1 Zn(CH$_3$)$_2$ | — | 700 | 96 | 462 |
| 10 | TaCl$_5$ | .66 Al(CH$_3$)$_3$ | Trace | 700 | 94 | 228 |
| 11 | TaCl$_5$ | .66 Al(CH$_2$CH$_3$)$_3$ | 0.300 | 700 | 84 | 53 |
| 12 | TaCl$_5$ | 2 MAO[f] | 0.112 | 700 | 84 | 314 |

Conditions: 0.050 mmol TaCl$_5$; 10 mL chlorobenzene solvent; 4 h reaction time; reaction temperature = 45° C.; 125 mL stainless steel, glass-lined autoclave.
[a]Calculated for 1-hexene only.
[b]0.5 mmol TaCl$_5$ and reaction temperature = 60° C.
[c]0.14 mmol TaCl$_5$ and reaction temperature = 60° C.
[d]0.1 mmol TaCl$_5$ and reaction temperature = 60° C.
[e]reaction in 10 mL toluene solvent.
[f]MAO = methylaluminoxane alkylating component.

What is claimed is:

1. A process for trimerizing ethylene, which comprises: reacting ethylene, at a temperature of from about 0° C. to about 100° C. and an ethylene pressure of from about 200 psig to about 1500 psig, using a catalytically effective amount of a catalyst composition comprising a tantalum compound and an alkylating component comprising a metal-containing compound selected from the group consisting of metal hydrocarbyl compounds, metal hydrocarbyl halide compounds and alkylaluminoxanes, such that a reaction product is formed, said reaction product comprising at least about 50 mole percent 1-hexene, based on the composition of the reaction product.

2. The process according to claim 1, wherein said tantalum compound is selected from the group consisting of tantalum halides, wherein the reaction temperature is from about 25° C. to about 70° C., and wherein said ethylene pressure is from about 500 psig to about 1000 psig.

3. The process according to claim 1, wherein said tantalum compound is selected from the group consisting of tantalum chloride and tantalum bromide, wherein the reaction temperature is from about 40° C. to about 60° C., and wherein said ethylene pressure is from about 500 psig to about 1000 psig.

4. The process according to claim 1, wherein the reaction product comprises at least 80 mole percent 1-hexene.

5. The process according to claim 2, wherein the reaction product comprises at least 80 mole percent 1-hexene.

6. The process according to claim 1, wherein the reaction product comprises at least 94 mole percent 1-hexene.

7. The process according to claim 2, wherein the reaction product comprises at least 94 mole percent 1-hexene.

8. The process according to claim 1, wherein said alkylating component is selected from the group consisting of tetramethyl tin, tetraethyl tin, dimethyl zinc, methyl lithium, trimethyl aluminum, n-butyl lithium, allyl triphenyl tin, triethyl aluminum, dimethyl aluminum chloride, tetraphenyl tin, methylaluminoxane, and methyl magnesium bromide.

9. The process according to claim 2, wherein said alkylating component is selected from the group consisting of tetramethyl tin, tetraethyl tin, dimethyl zinc, methyl lithium, trimethyl aluminum, n-butyl lithium, allyl triphenyl tin, triethyl aluminum, dimethyl aluminum chloride, tetramethyl tin, methylaluminoxane, and methyl magnesium bromide.

10. The process according to claim 4, wherein said alkylating component is selected from the group consisting of tetramethyl tin, tetraethyl tin, dimethyl zinc, methyl lithium, trimethyl aluminum, n-butyl lithium, allyl triphenyl tin, triethyl aluminum, dimethyl aluminum chloride, tetraphenyl tin, methylaluminoxane, and methyl magnesium bromide.

11. The process according to claim 7, wherein said alkylating component is selected from the group consisting of tetramethyl tin, tetraethyl tin, dimethyl zinc, methyl lithium, trimethyl aluminum, n-butyl lithium, allyl triphenyl tin, triethyl aluminum, dimethyl aluminum chloride, tetraphenyl tin, methylaluminoxane, and methyl magnesium bromide.

* * * * *